United States Patent [19]

Yamashita et al.

[11] Patent Number: 5,120,978
[45] Date of Patent: Jun. 9, 1992

[54] METHOD AND APPARATUS FOR SCATTERED LIGHT MEASUREMENTS

[75] Inventors: Tomoyoshi Yamashita; Yasuteru Tahara, both of Otake, Japan

[73] Assignee: Mitsubishi Rayon Co., Ltd., Kyobashi, Japan

[21] Appl. No.: 583,862

[22] Filed: Sep. 17, 1990

[30] Foreign Application Priority Data

Sep. 20, 1989 [JP] Japan .................. 1-244778

[51] Int. Cl.⁵ ............................................. G01N 21/86
[52] U.S. Cl. ....................... 250/571; 356/339
[58] Field of Search ............... 250/571, 563, 560, 561; 356/339, 340, 371, 446

[56] References Cited

U.S. PATENT DOCUMENTS

| | | | |
|---|---|---|---|
| 4,896,961 | 1/1990 | Ho ........................................ | 356/339 |
| 4,975,237 | 12/1990 | Brown ................................. | 356/339 |
| 4,990,795 | 2/1991 | Suzuki et al. ....................... | 356/339 |
| 5,017,008 | 5/1991 | Akiyama ............................. | 356/339 |

Primary Examiner—David C. Nelms
Assistant Examiner—K. Shami
Attorney, Agent, or Firm—Ladas & Parry

[57] ABSTRACT

A method and an apparatus for high-precision scattered light measurements characterized in that:

in the optical path of a laser beam from the laser light source, the cross section of the laser beam is adjusted, and the laser beam is irradiated into a specimen fixed relatively to the laser beam to cause scattered lights to be scattered from the specimen;

the angular distribution of the scattered lights is measured by adjusting the cross section for observing the scattered light in the optical path of the scattered light and scanning relatively with the specimen as its center; and by obtaining rapid and minute changes in the scattering intensities against minute changes in the scattering angles caused by the minute ununiformity in the structure of the specimen, the optical characteristics of transparent materials are evaluated.

5 Claims, 10 Drawing Sheets

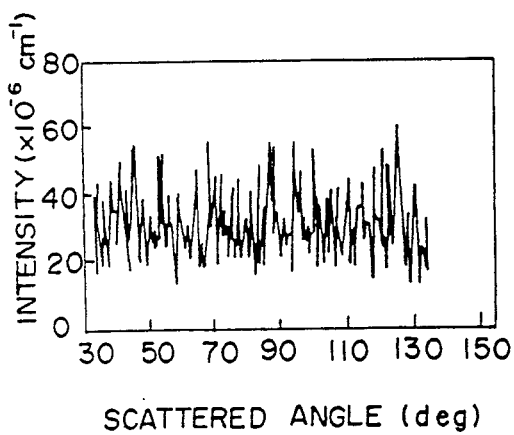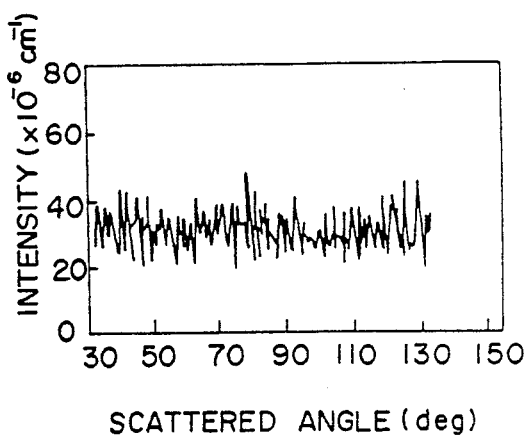
FIG.4(a)  FIG.4(b)
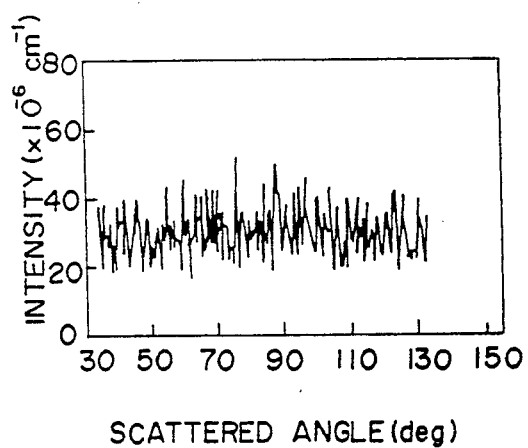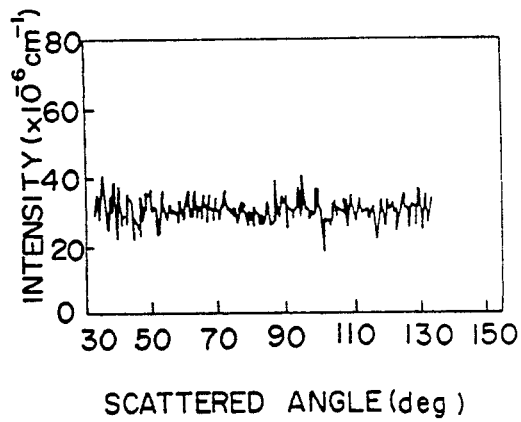
FIG.4(c)  FIG.4(d)

METHOD AND APPARATUS FOR SCATTERED LIGHT MEASUREMENTS

BACKGROUND OF THE INVENTION

1. Technical Field

The present invention relates to a method for scattered light measurements and an apparatus applicable thereto whereby a laser light is irradiated onto a transparent solid specimen to perform characteristic measurements by measuring the scattered lights being scattered from the specimen. Here a glass which is below the transition point (Tg) is also included in the transparent solid specimens.

2. Background Art

There is available an apparatus for measuring scattered lights of polymethyl methacrylate (PMMA) which is a typical transparent material for optic fibers and lenses (Otsuka et al [Papers on High Polymer]p. 266, No. 4, Volume 42 (1985)) shown in FIG. 10, for example, as an apparatus for the scattered light measurements to obtain scattered light data by measuring scattered lights being scattered from a specimen when a laser light is irradiated onto a transparent specimen available in various forms, such as gas, liquid, solution, and solid. The measuring method applicable to this apparatus is dependent on angles at intervals of several degrees (Otsuka et al [Preparatory Papers B for the Textile Society Symposium]B-p. 36, Jun. 1988, Textile Society).

From the scattered light profiles obtained using the above-mentioned apparatus, the Rayleigh scattering intensity (R) obtainable by the density fluctuations of the specimen is evaluated by the mean scattered light level in the wide angle region and its smooth distributive state, and in addition, from the profile in the lower angle region, the relative length which reflects the fine structure of the specimen is evaluated using the Debye plots.

[PROBLEMS TO BE SOLVED BY THE INVENTION]

As set forth above, the Rayleigh scattering intensities (R) obtainable by the density fluctuations of a transparent material and the relative length reflecting the fine structure thereof can be evaluated by the conventional apparatus and method. However, it is still difficult to measure the optical characteristics of transparent materials more precisely in order to evaluate the transparent optical materials from the new point of view.

SUMMARY OF THE INVENTION

The object of the present invention is to provide a method and an apparatus for scattered light measurements whereby a new knowledge and information of the structures of transparent materials can be acquired to evaluate the optical characteristics of the materials, making it possible to develop new highly capable optical materials.

[MEANS TO SOLVE THE PROBLEMS]

In order to achieve the above-mentioned object, the inventors and others carried out various researches and developments. Conventionally, it has been considered that if the optical purity is increased by removing impurities, such as dust and others, in an optical material to a certain extent, the angular distribution of scattered light intensities of the material represents a smooth curve, and when such smooth curve is not obtained, the results are neglected as simple non-reproducible noises that may have been caused by the insufficient accuracy of the apparatus in use. However, the inventors have come to know that even among those unsmooth curves of angular distributions (spiky representations of angular distribution curves), which have very good reproductivities under the high-precision light scattering measurements, there should be some which suggest new optical characteristics not known to public conventionally.

As a result of the further researches and developments, the inventors have discovered that if a scattering volume (V) and the broadening of the light receiving angle ($\Delta\theta$) are made the smallest possible for observation using a coherent laser light so as to investigate the ideal scattering profiles, it becomes possible to obtain a spiky scattered light distribution where the scattered lights from the minute region interfere with each other, and that the amplitude and the state of distribution show a close relationship with the ununiformity in the non-crystalline structures. Hence the present invention is completed.

In this specification, the "scattering volume V" and the "broadening of the light receiving angle $\Delta\theta$" in the case of the observation at an angle of substantially 90° to the incident direction are defined as follows with reference to FIG. 3:

$$\Delta\theta = \tan^{-1}\left(\frac{r_1 + r_2}{2l_2}\right) \quad (1)$$

$$V = \frac{\pi}{4} r_0^2 \left\{\frac{l_1}{l_2}(r_1 + r_2) + r_1\right\} \quad (2)$$

In the above equations and FIG. 3, the laser beam 31 is being passed through a specimen (not shown), and the lights scattered from that position are passed through the first pin hole 32 and second pin hole 33 to reach the light receiving device 34. The cross-sectional diameter of the laser beam 31 is $r_0$, the diameters of the first pin hole 32 and second pin hole 33 are $r_1$ and $r_2$ respectively, the distance between the central axis of the laser beam and the first pin hole is $l_1$, and the distance between the first pin hole and second pin hole is $l_2$. In this case, the angle of receiving light is substantially 90°. The scattering volume V is shown with slashes.

In the above case, if the sizes of the first and second pin holes are equal, i.e., if the expression $r_1 = r_2 = r$ is established, the definitions are particularly $r_2 = r$ is established, the definitions are particularly made in accordance with the following equation:

$$\Delta\theta = \tan^{-1}\left(\frac{r}{l_2}\right) \quad (1')$$

$$V = \frac{\pi}{4} r_0^2 r \left(2\frac{l_1}{l_2} + 1\right) \quad (2')$$

According to the present invention, the aforementioned measuring condition should be such that the scattering volume is 1 mm$^3 \geq$ V $>$ 0, preferably $10^{-1}$ mm$^3 \geq$ V $>$ 0, still more preferably $10^{-2}$ mm$^3 \geq$ V $>$ 0, or most preferably $10^{-3}$ mm$^3 \geq$ V $>$ 0. If the condition exceeds the above-mentioned uppermost limit, information from the minute local part of the structure becomes so much that only averaged scattering profile is obtained. As the V value becomes smaller, the optical quantity is reduced. However, this reduction can be compensated with a prolonged measuring time. It is desirable to define a specific set value for the scattering volume in consideration of the properties of a specimen, the broadening of the light receiving angle $\Delta\theta$, and others.

The broadening of the light receiving angle should desirably be the narrowest possible; it should be, for example, 0.5 deg $\geq \Delta\theta > 0$, still more preferably 0.1 deg $\geq \Delta\theta > 0$, or most preferably 0.05 deg $\geq \Delta\theta > 0$. This is because of the fact that if the angular broadening exceeds the above-mentioned uppermost limit, the resolution is lowered to make it impossible to obtain high-precision scattering profiles. As the value becomes smaller, the quantity of the scattered light is reduced. However, this reduction can be compensated with a prolonged measuring time. It is desirable to define a specific set value for the broadening of the light receiving angle in consideration of the properties of a specimen, the scattering volume V, and others.

In any event, these measuring conditions must be defined so as to obtain the sudden and minute changes in the scattering intensities (the spiky scattering phenomena) caused by the minute ununiformity in the structures of transparent noncrystalline specimens.

[FUNCTION]

With the constituents set forth above, the present invention functions as follows:

Usually, in the case of observing a scattering phenomenon, taking that the measurement of the scattering light at an angle $\theta$ is meant to measure the data of the scattered light for $\theta \pm \Delta$. Here the $\pm\Delta$, i.e., the broadening of the light receiving angle defined in the previous description, results from an optical solid angle $\omega$ and corresponds to an optical resolution.

Hence if the broadening of the light receiving angle can be made the smallest possible ($\Delta\theta \rightarrow 0$), the measuring resolution is increased so as to represent a state closest to the ideal scattering profile.

However, even when the resolution is increased by making the $\Delta\theta$ smaller to a certain extent, the ideal speckle width, not things observed practically, becomes narrower accordingly if the scattering volume V is great. This results in a lower resolution after all against the observation angle of $\Delta\theta$.

According to the present invention, both $\Delta\theta$ and V are so defined that they are made the smallest possible to acquire information about scattering conditions having the following characteristics caused by the local structures of transparent noncrystalline specimens:

There are minute and sudden changes in scattering intensities (laser speckles) against minute changes in the scattering angles.

There are observed fluctuations of long cycles in the scattering profiles.

There are various other representations of different kinds of periodicities.

Normally, the background scatterings and the laser speckles (i.e., providing statistics of intensity histogram in accordance with the speckle theory) are separated.

The scattering profiles show high reproducivities.

The scattering profiles are caused by the interior structures of the transparent noncrystalline specimens.

From the above scattering profiles, the following information about the interior structures of the transparent noncrystalline specimens can be acquired:

① The existence of optical impurities (dust, catalyst, heterogeneous structures) remaining in the specimen are determined qualitatively, and with other means, it can be measured quantitatively.

② The ununiformity by the region of micron or submicron order of an important optical transparent non-crystalline material is qualitatively analyzed for its quantitative evaluation.

③ The critical value of the light scattering loss characteristic to a specimen can be estimated.

④ In the substantial fluctuations of a transparent material, the contributions of the dynamic fluctuations $\phi_{dyn}$ (equilibrium) and the static fluctuations $\phi_{qst}$ non-equilibrium) are separated and defined respectively.

⑤ The isothermal compressibility of a material accompanying the dynamic fluctuation $\phi_{dyn}$ can be evaluated without any contacting.

According to a first aspect of the present invention, there is provided a high-precision scattered light measuring method characterized in that:

in the optical path of a laser beam from the laser light source, the cross section of the laser beam is adjusted, and the laser beam is irradiated into a specimen fixed relatively to the laser beam to cause scattered lights to be scattered from the specimen;

in the optical path of the scattered light, the cross section for observing the scattered light is adjusted to measure the angular distribution of the scattered lights by scanning relatively with the specimen as the center thereof; and by obtaining the rapid and minute changes in the scattered intensities of the scattering angle caused by minute ununiformity in the structure of the transparent specimen, the optical characteristics of the transparent materials are evaluated.

Also, according to a second aspect of the present invention, there is provided a high-precision scattered light measuring method for evaluating the optical characteristics of transparent materials in the above-mentioned first aspect, wherein the measuring conditions are defined to provide a given scattering volume and a given broadening of light receiving angle by adjusting the cross sections of said incident laser beam and scattered light.

Furthermore, according to a third aspect of the present invention, there is provided a high-precision scattered light measuring method for evaluating the optical characteristics of transparent materials having the scattered light measuring method wherein:

in the optical path of a laser beam from the laser light source, the cross section of the laser beam is adjusted, and the laser beam is irradiated into a specimen fixed relatively to the laser beam to cause scattered lights to be scattered from the specimen; and in the optical path of the scattered light, the cross section for observing the scattered light is adjusted to increase the resolution accuracy for the observation, and the angular distribution of the scattered lights is measured by scanning relatively to the center of the laser beam in a specimen; characterized in that:

the measuring conditions are defined to provide the scattering volume of 1 mm$^3$ or less (V: in the case of observation at an angle of substantially 90° to the incident direction) and the broadening of the light receiving angle (Δθ) of 0.5 deg or less by adjusting the cross sections of the incident laser beam and scattered light.

Furthermore, according to a fourth aspect of the present invention, there is provided a high-precision scattered light measuring apparatus for evaluating the optical characteristics of transparent materials comprising a laser light source irradiating a laser beam into a specimen, a specimen supporting member fixing the specimen relatively to the laser beam, a scattered light measuring member for measuring the angular distribution of the scattered light by scanning relatively with the specimen as its center, and beam adjusters for adjusting the cross section of the incident laser beam and the cross section for observing the scattered light; characterized in that:

the beam adjusters comprise an incident laser beam adjuster provided in the optical path of the laser beam to adjust the cross section thereof, and a scattered light adjuster provided in the optical path between the specimen and the scattered light measuring member to adjust the cross section for observing scattered light; and the beam adjusters define the measuring conditions to provide the scattering volume of 1 mm$^3$ or less (V: in the case of observation at an angle of substantially 90° to the incident direction) and the broadening of the light receiving angle of 0.5 deg or less (Δθ).

BRIEF DESCRIPTION OF THE DRAWINGS

FIGS. 4(a)-(d) are views showing scattered profiles of spiky scattering variations resulting from changes in the V and Δθ;

DETAILED DESCRIPTION OF THE PREFERRED EMBODIMENT

Although the present invention will subsequently be described in detail with reference to the preferred embodiment thereof, it is to be understood that the present invention is not limited to the example stated below unless it departs from the purport of the present invention.

Figure 1:
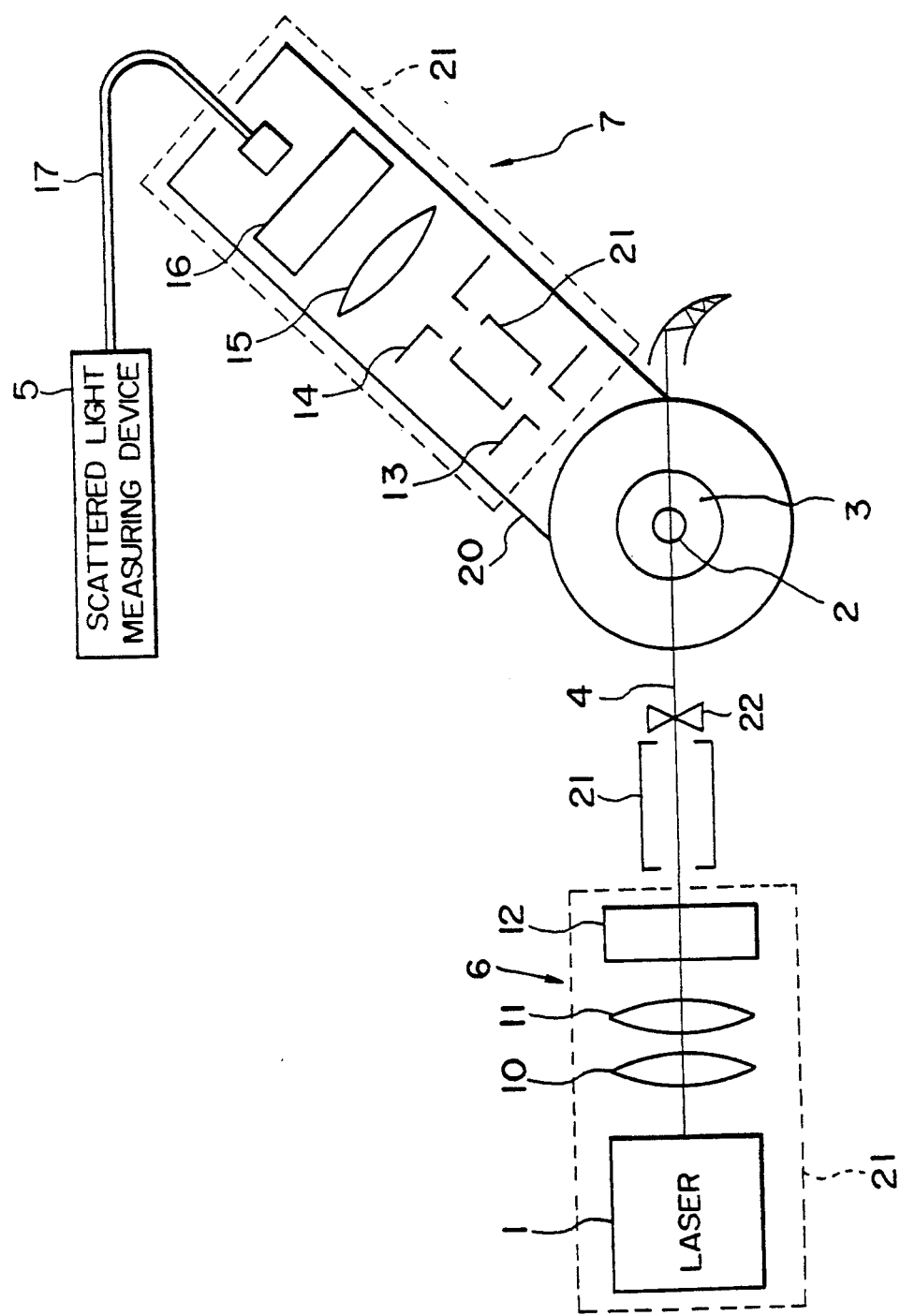
FIG. 1 is a schematic view showing an example of a light scattering apparatus according to the present invention.
Figure 2:
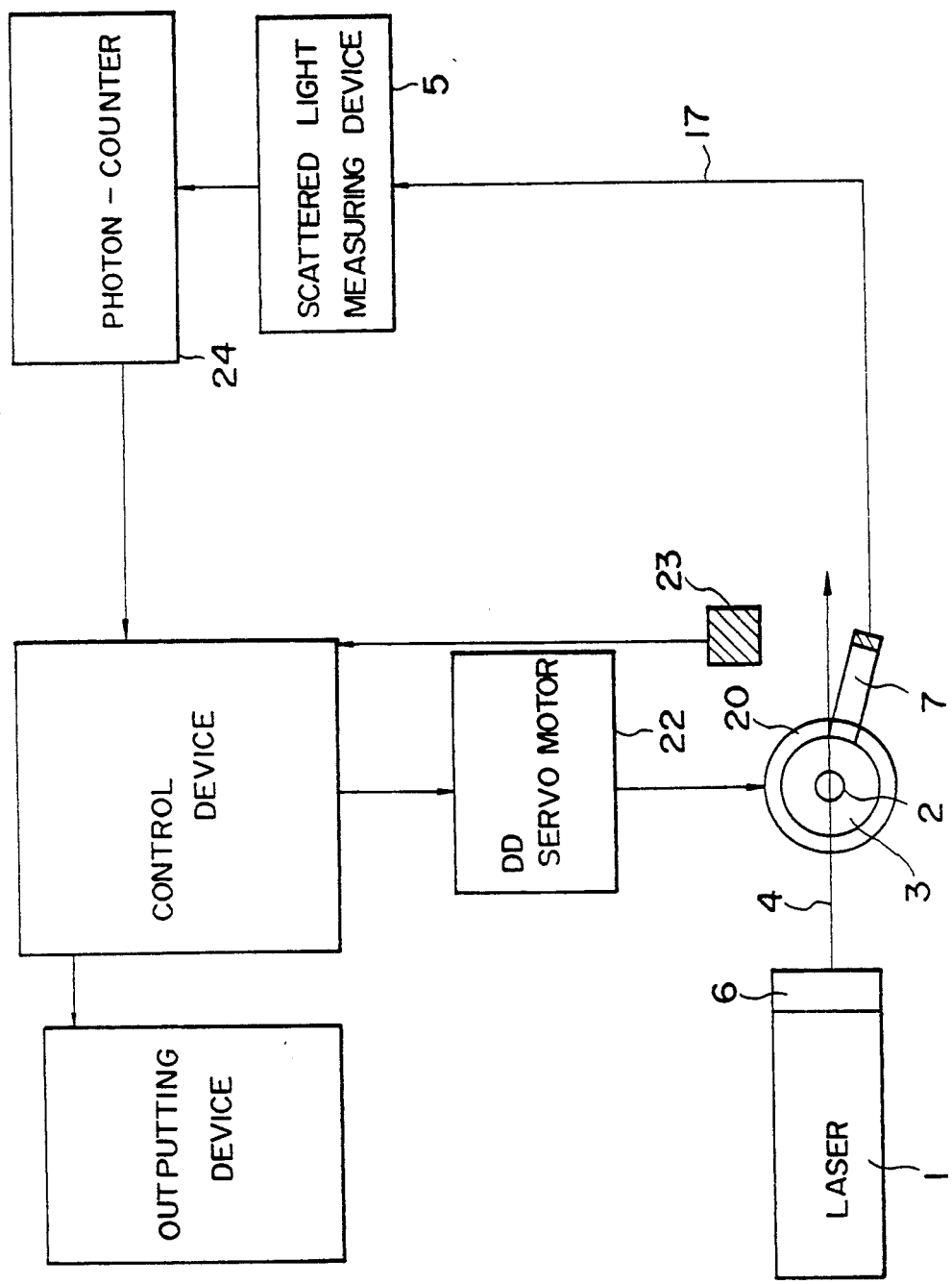
FIG. 2 is a block diagram showing a light scattering apparatus according to the present invention.
Figure 3:
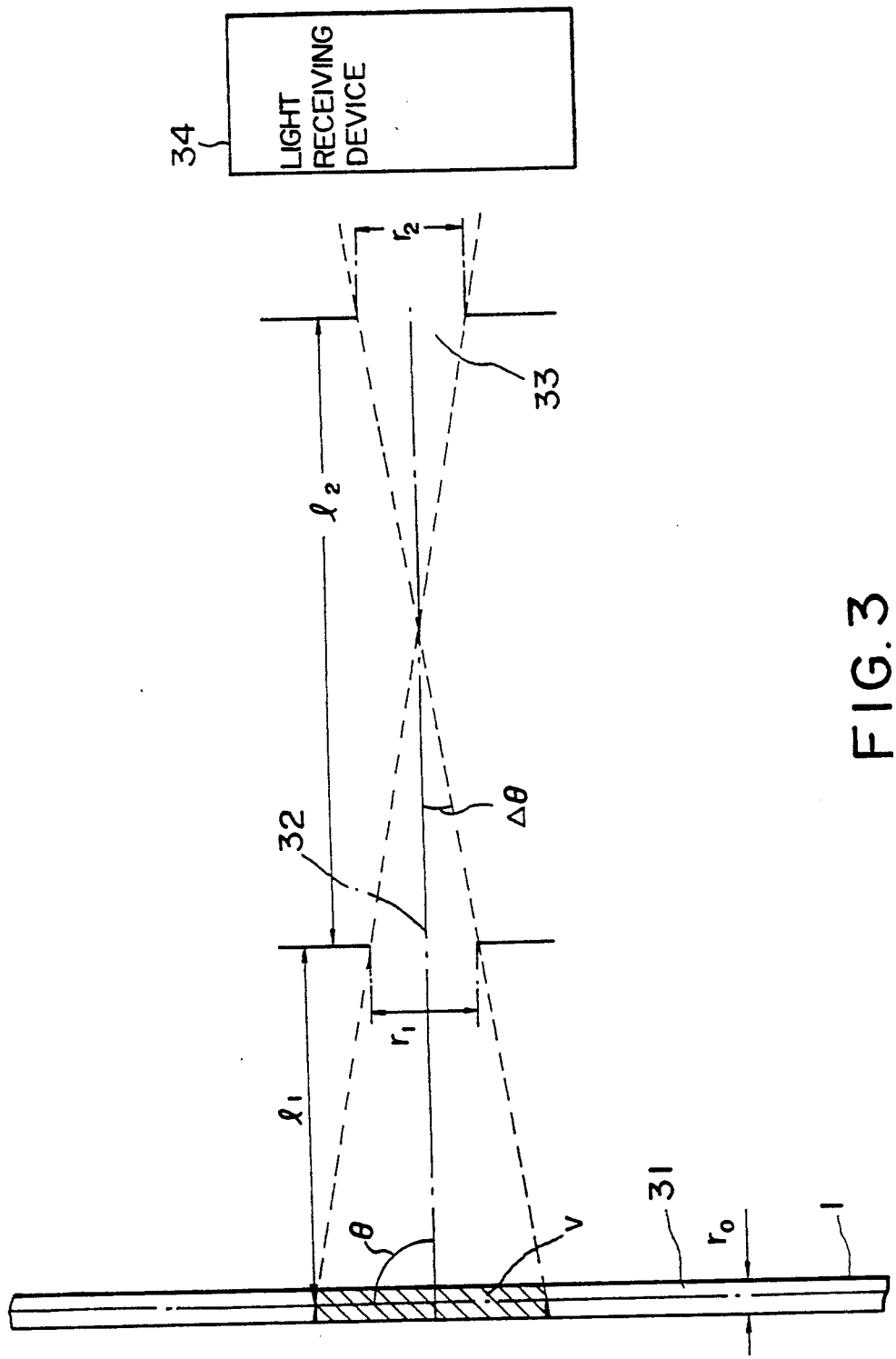
FIG. 3 is a typical representation illustrating the scattering volume V and the broadening of the light receiving angle Δθ.

A block diagram representation of an example of the apparatus used for a scattered light measuring method according to the present invention is shown in FIG. 2, and the optical system for the apparatus is shown in FIG. 1.

In this example, the apparatus comprises an Ar ion-laser light source 1 (manufactured by NEC) irradiating into a specimen 2 an Ar laser beam 4 having wavelength of 488 nm, a specimen stand 3 (a device holding a specimen) on which the specimen 2 is mounted in such a manner that the specimen 2 is fixed relatively to the laser beam 4, a scattered light measuring device 5 to measure the angular distribution of the scattered lights, an incident laser beam adjuster 6 which is provided in the optical path of the laser beam 4 to adjust the cross section of the laser beam, and a scattered light beam adjuster 7 which is provided in the optical path between the specimen 2 and the scattered light measuring device 5 to adjust the cross section for observing the scattered light.

In this embodiment, the incident laser beam adjuster 6 comprises two condenser lenses 10 and 11, and a polarizer 12 to narrow down the laser light from the lighting source 1 to a thin parallel laser light with a cross-sectional diameter of approximately 10–1,000 μmφ, preferably 50–700 μmφ, or still more preferably 200 μmφ or less.

The scattered light beam adjuster 7 comprises two pin holes 13 and 14 (the diameter is 0.6 mmφ and the distance between the pin holes, 128 mm, for example), a condenser lens 15 and horizontal and vertical polarizing plates 16 in order to adjust the scattered light to have a given cross section for observing scattered light.

In the down stream of the light passing through the polarizing plate 16, an incident terminal of an optical fiber 17 is arranged, and the scattered light measuring device 5 is mounted on the irradiation terminal thereof, i.e., the other end of this optical fiber 17, to scan rotatably around the laser beam in the specimen as its center.

The scattered light measuring device 5 of this embodiment comprises a photomultiplier (its applied voltage—1,150 V) to measure a luminous energy by increasing S/N ratio using a photoelectric computation made by a photon-counter with a built-in level sampling discriminator (manufactured by Hamamatsu Photonics Co., Ltd.) and a digital lock-in method by using an up-down counting system synchronized with a light chopper 22.

The specimen 2 is mounted on the specimen stand 3 (a device holding the specimen) and is fixed relatively to the laser beam 4.

The scattered light beam adjuster 7 is mounted by magnet on an arm 20 (in a place 400 mm away from the center, for example), which is arranged on the outer circumference of a rotary stage rotating with the central axis of the specimen (making right angles to the laser beam) as its center.

For the apparatus according to this embodiment, there are provided optical shielding 21, each for the entire optical path in the light receiving section and the light source to shield each of them from the external light.

A DD servo motor 22 (manufactured by Yokogawa Precision Co., Ltd.) is installed in the rotary stage to allow the scattered light measuring member to scan rotatably around the specimen as its center. This servo motor is capable of performing a high-precision rotational positioning with its built-in optical encoder generating 1,024,000 pulses per revolution to achieve the repeatability of ±2 sec (1/800 deg) or more and the positioning precision of 30 sec (1/120 deg).

In order to set up a rotational coordinate, a proximity switch 23 (manufactured by Tateishi Electric Mfg. Co., Ltd.) is employed as a positioning sensor for determining the home position for the motor. With the output signals from this sensor and the encoder, a highly precise positioning of the home position can be performed by an external control.

In the beam adjuster of the apparatus abovementioned, measuring conditions are adjusted to provide a scattering volume (V) of 1 mm³ or less and/or the broadening of the light receiving angle ($\Delta\theta$) of 0.5 deg or less in the case of the observation at an angle of substantially 90° to the incident direction.

APPLICATION EXAMPLE

A scattered light measuring method according to the present invention will subsequently be described in detail using the apparatus of this embodiment.

A specimen must first be prepared. The specimen can be, for example, a transparent noncrystalline material, such as inorganic glass and polymethylmethacrylate (PMMA), a transparent crystalline material such as crystal, and a translucent material.

Provided that the scattered light measurement is applicable, any specimens can be used irrespective of its contours and the states thereof, such as solid, liquid, or gas. As a specific contour, the specimen can be cylindrical, conic, cylindrical rod, filamentary, spherical, drum-shape, spindle-shape, etc., and its contour is so selected that the radially scattered light from a micro scattering volume in the center of the specimen always crosses vertically from the lateral face of the specimen.

In preparing a specimen, it is desirable to carry out a pre-processing so as to eliminate any possible effects caused by the condition of its lateral face by, for example, immersing it in a matching oil having the same refractive index as the specimen or by coating such matching oil on the surface of the specimen. The specimen thus prepared is mounted on the specimen stand. As to the matching oil, silicone oil, dibutyl phthalate and others are applicable.

The cross section of a laser beam is adjusted and polarized in the incident laser beam adjuster 6 provided in the optical path from the laser light source, and the laser beam thus adjusted and polarized is irradiated into the specimen fixed relatively to the laser beam.

By this incidence, the scattered light is being scattered beginning with the condition that the scattering volume of the specimen is 1 mm³ or less when it is observed at an angle of substantially 90° to the incident direction.

In the optical path of the scattered light, the cross section for observing the scattered light is adjusted, and angular distribution of the scattered lights is measured by allowing the scattered light measuring member to rotatably scan relatively with the specimen as its center.

This measurement is taken by measuring the scattering intensities Vv and Hv when each of them is scattered with the respective vertical and horizontal polarizing elements. By use of the photon-counter 24, the optical quantity is measured by the photo-electronic computation. The count time is approximately 2 seconds at a point, for example, and it can arbitrarily selected for changes in accordance with the other conditions.

In the above example, with the adjustments of the cross sections of the incident laser beam and scattered light, the measuring condition is established to be the scattering volume of 1 mm³ or less (V: in the case of the observation at an angle of substantially 90° to the incident direction) and/or the broadening of the light receiving angle ($\Delta\theta$) of 0.5 deg or less.

It is to be understood that the present invention is not limited to the example set forth above, and various changes and modifications are possible without departing from the purport thereof.

An example of a high-precision scattered light measuring method will subsequently be described with reference to the application of the apparatus according to the above-mentioned embodiment.

EXPERIMENTAL EXAMPLE 1

A cylindrical rod type specimen of 18 mm$\phi$ diameter and approximately 20 mm$\phi$ long taken from a preform fused quartz for an optical fiber was immersed in a matching oil comprising silicone oil.

This fused quartz specimen was precisely measured by use of the high resolution scattered light measuring apparatus shown in FIGS. 1 and 2.

In this respect, the distance $l_1$ between the central axis of the laser beam and the first pin hole was 74 mm and the distance $l_2$ between the first pin hole and the second pin hole was 128 mm.

By the beam adjuster, the diameters of the two pin holes were both adjusted to be 600 μm to 1,000 μm, and the diameter of the laser beam was modified to be approximately 150 μm to 600 μm using the two condenser lenses in the light source so as to adjust the optical cross sections of the incident laser beam and scattered light. As a result, the scattering profile was recorded under the measuring conditions stated below:

| Test Nos. | Measuring Conditions | |
| --- | --- | --- |
| | Pin Hole diameters | Laser beam diameters |
| a | 600 μm | 150 μm |
| b | 1,000 μm | 150 μm |
| c | 600 μm | 600 μm |
| d | 1,000 μm | 600 μm |

| | V ($\times 10^{-2}$ mm³) | $\Delta\theta$ (deg) |
| --- | --- | --- |
| a | 2.28 | 0.268 |
| b | 3.81 | 0.417 |
| c | 36.60 | 0.268 |
| d | 61.00 | 0.447 |

The results of the test Nos. a, b, c, and d are respectively shown in FIGS. 4(i a), (b), (c), and (d).

As shown in FIG. 4, the amplitudes of the spiky scattering profiles become greater as the resolution becomes higher in the order of d, c, b, and a, and it is obvious that the means scattering profile has changed into the scattering profile resulting from the interior structures which are extremely minute and local.

EXPERIMENTAL EXAMPLE 2

In order to verify the above-mentioned experimental example 1, a pure benzene solution, which was considered to be in a sufficiently uniform and non-structural state due to the time averaging by molecular movement, was applied to observing the scattered light profiles in the same way as in the above example under the measuring conditions stated below:

| Measuring Conditions | |
| --- | --- |
| Pin hole diameter | Laser beam diameter |
| 600 μm | 150 μm |

-continued

| Measuring Conditions | |
|---|---|
| Pin hole diameter | Laser beam diameter |
| $V (\times 10^{-2} mm^3)$ | $\Delta\theta$ (deg) |
| 2.28 | 0.268 |

Figure 5:
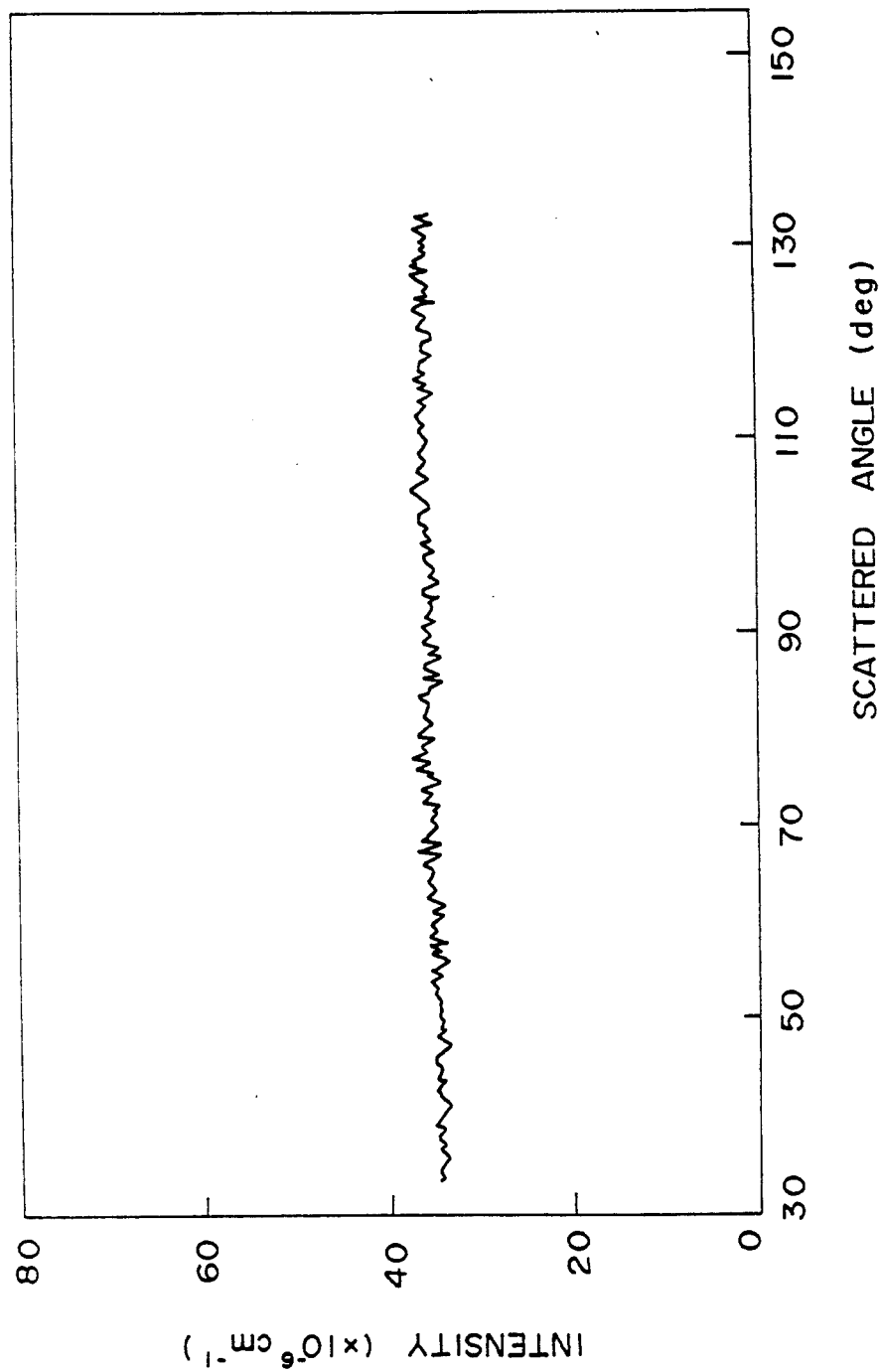
FIG. 5 is a view showing the scattering profile of the pure benzene.

The results are shown in FIG. 5. As obviously noticeable from that figure, the spiky scattering phenomena resulting from the ununiformity in the interior structure are not observed. Only extremely minute fluctuations are observed because of the simple noises generated by the detector in use.

EXPERIMENTAL EXAMPLE 3

A scattered light profile was observed using a high purity polymethyl methacrylate (PMMA manufactured by Mitsubishi Rayon Co., Ltd.) which was employed as a core material for a plastic optical fiber. The observation was made in the same way as in the previous example under the measuring conditions stated below:

| Measuring Conditions | |
|---|---|
| Pin hole diameter | Laser beam diameter |
| 600 μm | 150 μm |
| $V (\times 10^{-2} mm^3)$ | $\Delta\theta$ (deg) |
| 2.28 | 0.268 |

Figure 6:
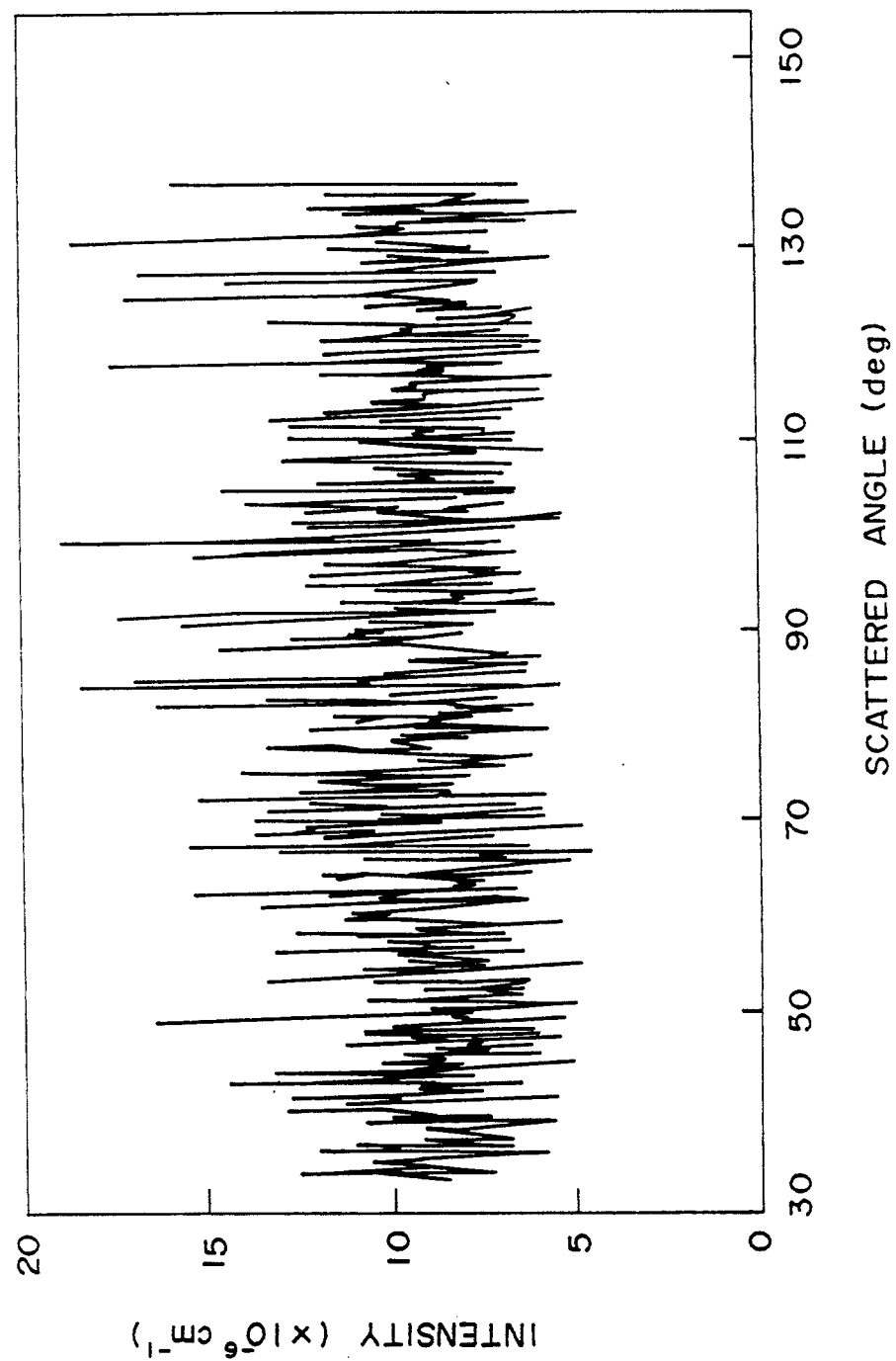
FIG. 6 is a view showing the spiky scattering profile of PMMA.

The results are shown in FIG. 6. As obviously noticeable from that figure, the spiky scattering phenomena caused by the ununiformity in the interior structure are observed. The reproducibility thereof is significantly high.

EVALUATION EXAMPLES

A transparent noncrystalline material was evaluated by the scattered light measuring method according to the present invention in relation to the amorphous structure (ununiform structure) of PMMA.

A PMMA rod was fixed in a sample cell with a heater, and its temperature was gradually raised under control by a temperature controller from 30° C., 70° C., 90° C., 110° C., and 130° C. Then it was lowered likewise. The scattered light was measured in a completely stable thermal condition when the thermal equilibrium was reached at each of these temperatures. The results are shown in FIG. 7.

Furthermore, a DSC measurement was carried out for this specimen. The results are shown in FIG. 8.

Figure 7:
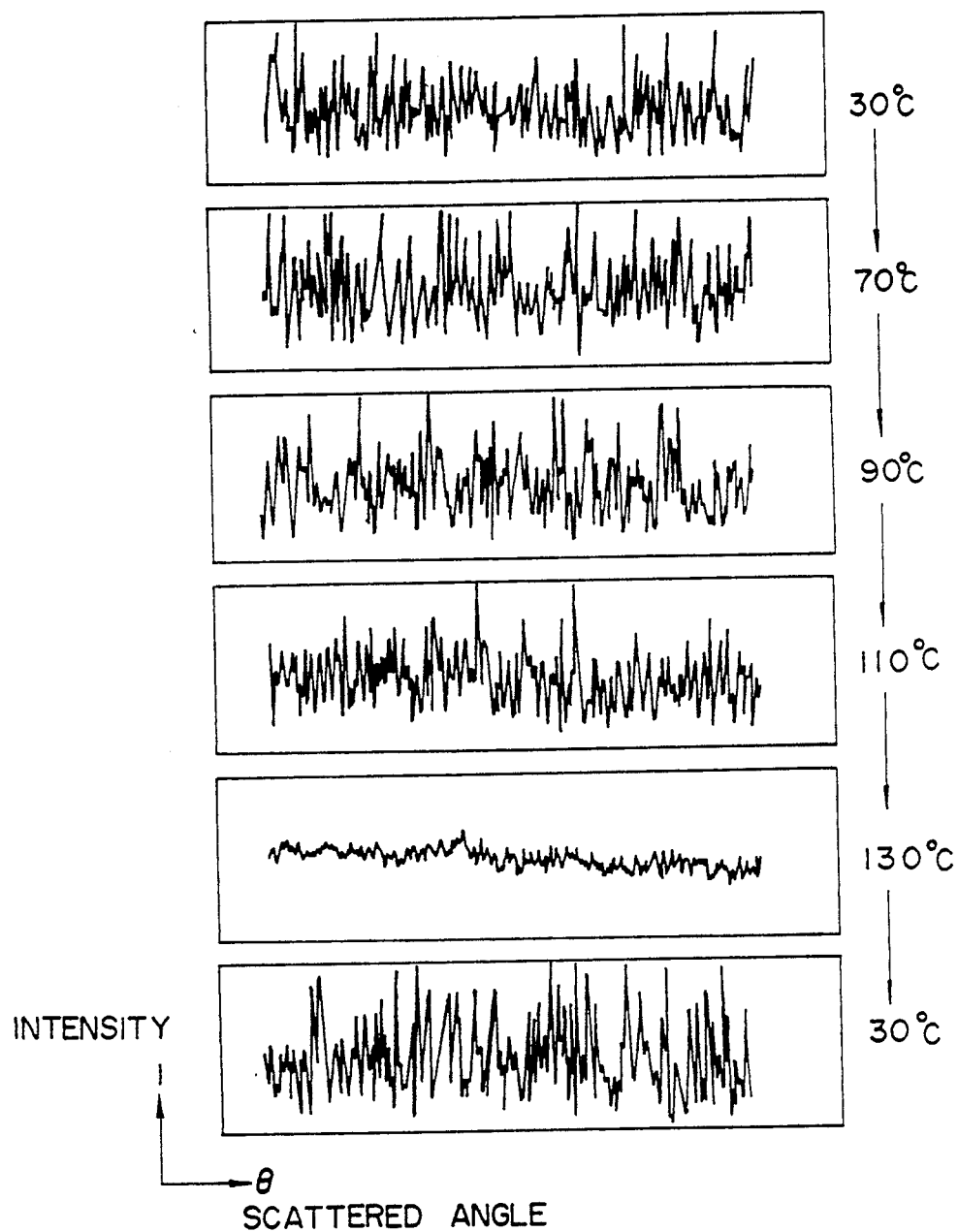
FIG. 7 is a view showing the spiky scattering profile of PMMA resulting from the temperature changes.

As obviously noticeable from the temperature changes in the scattering profile shown in FIG. 7, there is almost no change in the amplitudes of the scattered light up to 90° C. From 110° C., a tendency of reduction is slightly observed. Then at 130° C., it is rapidly reduced and the spiky scattering phenomenon suddenly disappears.

In the process of temperature drop, the spiky scattering phenomenon again appears in the vicinity of 110° C. and the same type of scattering is observed as in the process of temperature rise. In this respect, the profiles observed were not exactly the same before and after being heated.

Figure 8:
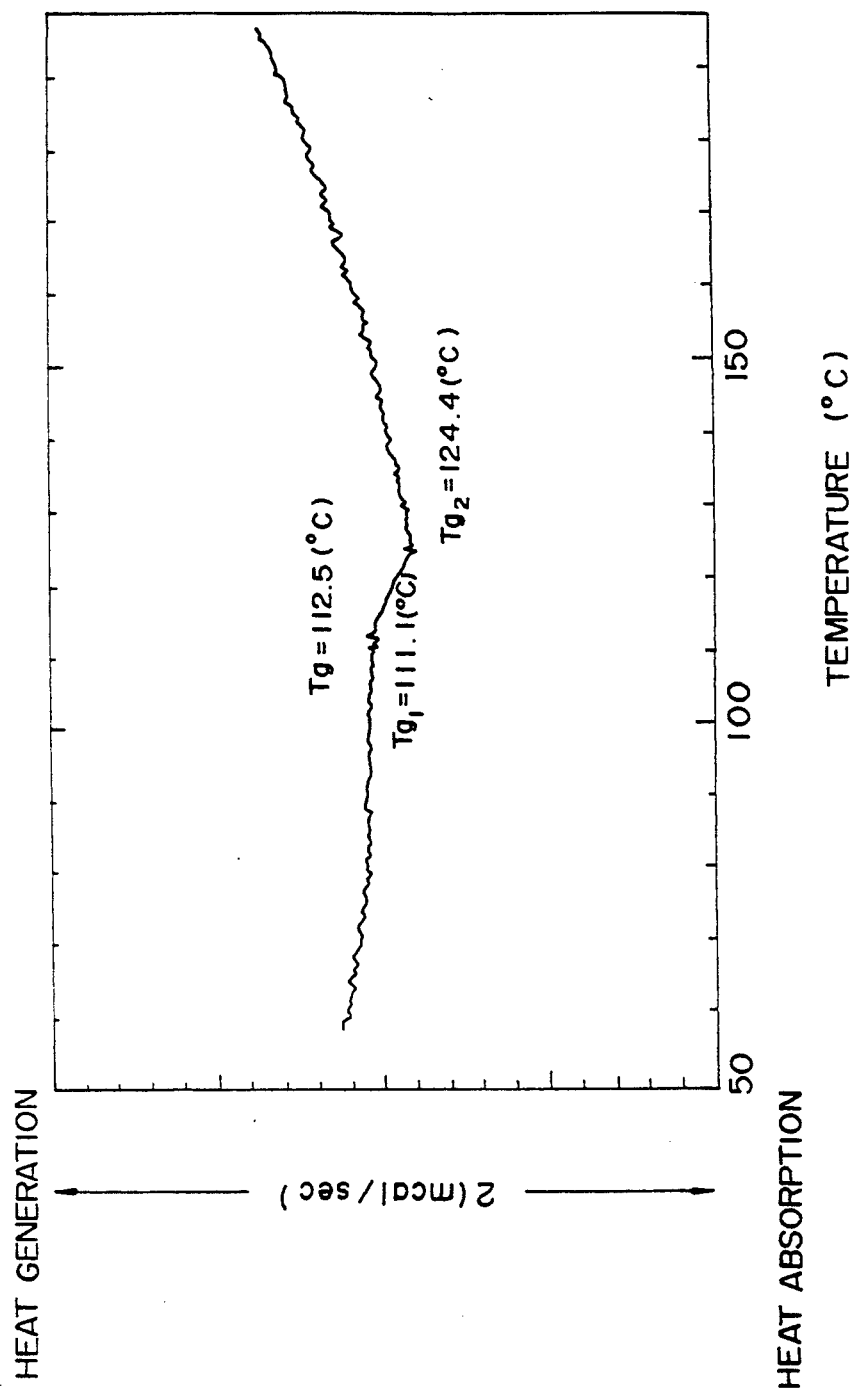
FIG. 8 is a view showing the resultant profile of DSC measurement of PMMA.

From the result of the DSC measurement shown in FIG. 8, it is obvious that the glass transition point (Tg) of PMMA is in the vicinity of 112.5° C., and that the spiky scattering disappears or appears reversibly with this glass transition point (Tg) as its boundary.

Figure 9:
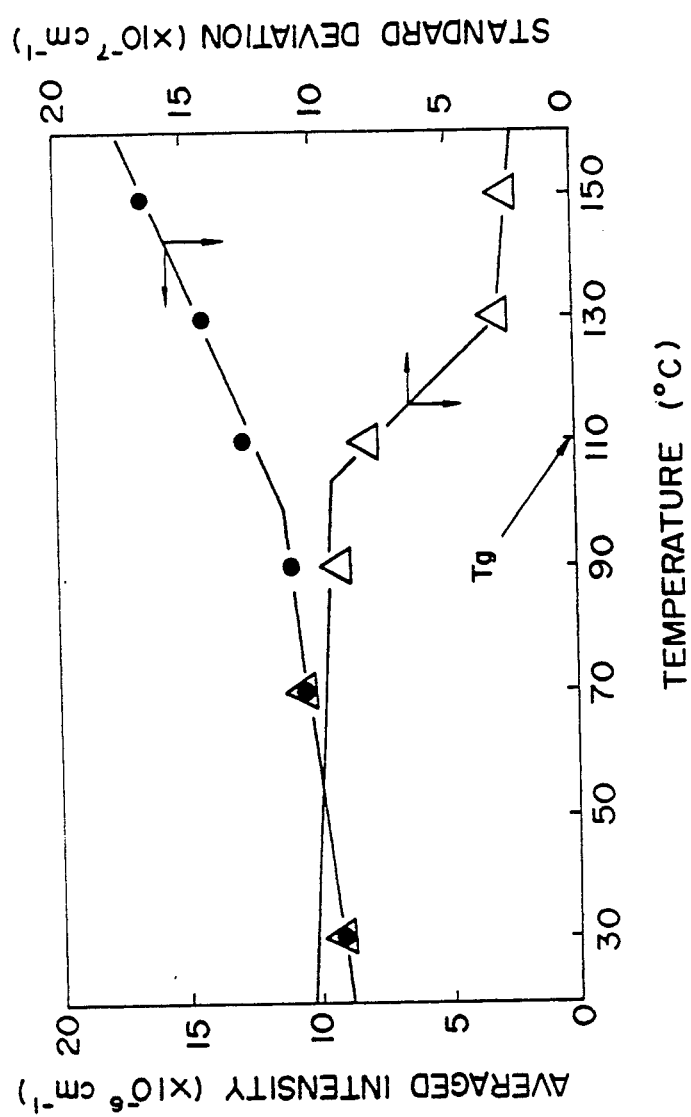
FIG. 9 is a graphic representation showing the variations of the standard deviation of the averaged scattering intensities and the spiky scatterings in accordance with the PMMA temperature changes.
Figure 10:
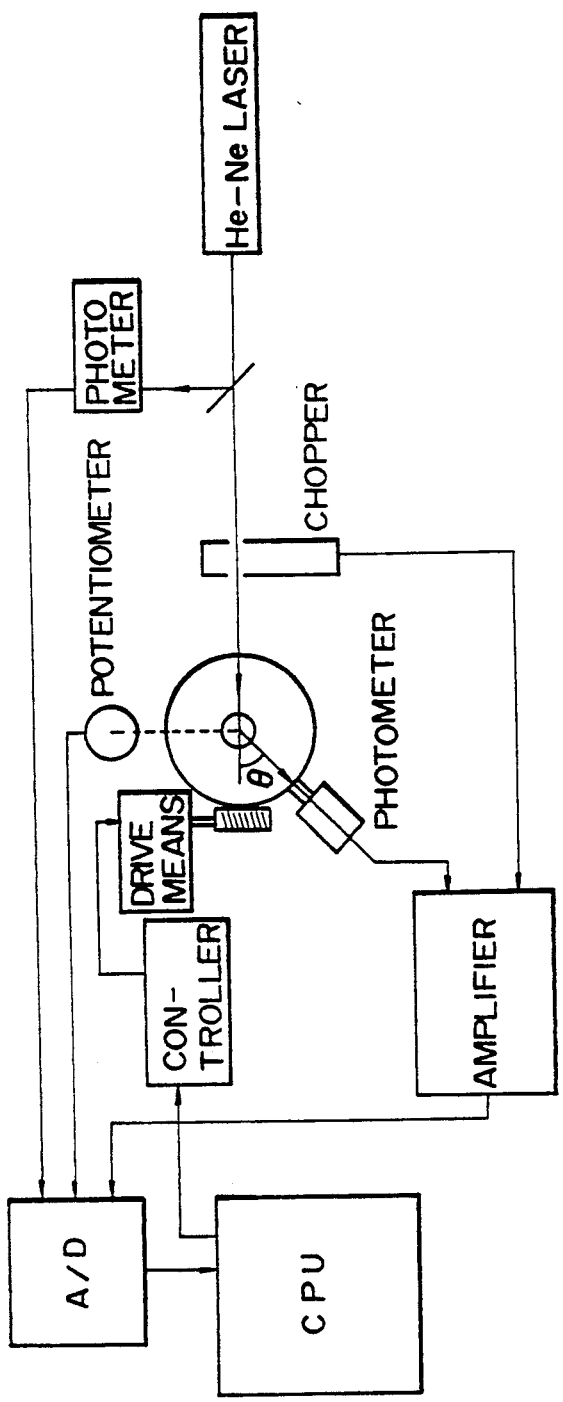
FIG. 10 is a schematic view showing a conventional apparatus for scattered light measurements.

Based on the above-mentioned data, a graph is shown in FIG. 9 where the sample temperatures (T) are given in the abscissa, the averaged intensities, in the ordinate on the left-hand side, and the standard deviations (averaged intensity of spiky scattering amplitudes), in the ordinate on the right-hand side.

In FIG. 9, the scattering intensities become greater in the temperature region of $T \geq Tg$ and the amplitudes become smaller. In the temperature region of $T < Tg$, there are not much changes observed against the respective temperatures.

This is considered attributable to the sudden reduction of the spiky scattering amplitudes in the temperature region of $T \geq Tg$ where the intensity becomes greater due to the increasingly promoted micro Brownian motion of polymer as the temperature increases, and the amorphous structures are observed to be in a uniform state more averaged timewise due to a sufficiently increased movability of the polymer with the temperature rise as compared with the observed time $\Delta t$. In the temperature region of $T < Tg$, the structure is almost in the frozen state and there are almost no changes in the averaged scattering intensities and scattering amplitudes. It is conceivable that ununiform structures in the amorphous polymer remaining in the frozen state are reflected for some reason as spiky scattering phenomena.

From the evaluation examples set forth above, it is verified that there is a close relationship between the structural phase transition before and after the glass transition point (Tg) of the PMMA which is a transparent noncrystalline material and the reversible disappearance and appearance of the spiky scatterings, so that the phase transition can be observed by the scattered light measuring method according to the present invention.

In other words, furthermore, the spiky scattering phenomena obtainable by this measuring method of the present invention reflect the ununiform structures of the transparent amorphous body, and by evaluating the phenomena, it is possible to evaluate the characteristics, features and natures of transparent noncrystalline materials.

[EFFECT OF THE INVENTION]

As verified by the above-mentioned samples, the method and apparatus according to the present invention can produce the effects as follows:

(1) By observing the spiky scattering profiles, the ununiformity in the interior structures of transparent noncrystalline materials can be evaluated as verified in the examples set forth above. In other words, the spiky scattering profile becomes acuter as the ununiformity is more prominent. A uniform profile is obtained as the structure becomes more uniform.

(2) With the scattering theory, the spiky scattering data obtained by the measurement according to the present invention can be analyzed to evaluate the ununiform structures of transparent noncrystalline materials theoretically.

Therefore, by measuring the above-mentioned spiky scattering phenomena, the new knowledge and view which have never been available conventionally can be acquired regarding the structures of transparent noncrystalline materials, and using the evaluating means of the present invention, optical materials, such as highly capable optical fibers, and optical lenses, can be developed.

What is claimed is:

1. A high-precision scattered light measuring method for evaluating the optical characteristics of transparent materials comprising
   in the optical path of a laser beam from the laser light source, the cross section of the laser beam is adjusted, and the laser beam is irradiated into a specimen fixed relatively to the laser beam so as to cause scattered lights to be scattered from the specimen;
   in the optical path of the scattered light, the cross section for observing the scattered light is adjusted to measure the angular distribution of the scattered lights by scanning relatively with the specimen as the center thereof, the measuring conditions are defined to provide a given scattering volume and a given broadening of light receiving angle by adjusting the cross sections of said incident laser beam and scattered light
   by obtaining the rapid and minute changes in the scattering intensities of the scattering angle caused by the minute ununiformity in the structure of a transparent specimen.

2. A high-precision scattered light measuring method for evaluating the optical characteristics of transparent materials having the scattered light measuring method comprising:
   in the optical path of a laser beam from the laser light source, the cross section of the laser beam is adjusted, and laser beam is irradiated into a specimen fixed relatively to the laser beam to cause scattered lights to be scattered from the specimen; and
   in the optical path of the scattered light, the cross section for observing the scattered light is adjusted to increase the resolution accuracy for the observation, and the angular distribution of the scattered lights is measured by scanning relatively to the center of the laser beam in a specimen;
   the measuring conditions are defined to provide the scattering volume of 1 $mm^3$ or less and the broadening of the light receiving angle ($\Delta\theta$) of 0.5 deg or less by adjusting the cross sections of the incident laser beam and scattered light.

3. A high-precision scattered light measuring apparatus for evaluating the optical characteristics of transparent materials comprising a laser light source irradiating a laser beam into a specimen, a specimen supporting member fixing the specimen relatively to the laser beam, a scattered light measuring member for measuring the angular distribution of the scattered lights by scanning relatively with the specimen as its center, and beam adjusters for adjusting the cross section of the incident laser beam and the cross section for observing the scattered light comprising:
   the beam adjusters comprise an incident laser beam adjuster provided in the optical path of the laser beam to adjust the cross section of the laser beam, and a scattered light adjuster provided in the optical path between the specimen and the scattered light measuring member to adjust the cross section for observing scattered light; and
   the beam adjusters define the measuring conditions to provide the scattering volume of 1 $mm^3$ or less and the broadening of light receiving angle 0.5 deg or less ($\Delta\theta$).

4. A high-precision scattered light measuring method for evaluating the optical characteristics of transparent materials having the scattered light measuring method comprising:
   in the optical path of a laser beam from the laser light source, the cross section of the laser beam is adjusted, and laser beam is irradiated into a specimen fixed relatively to the laser beam to cause scattered lights to be scattered from the specimen; and
   in the optical path of the scattered light, the cross section for observing the scattered light is adjusted to increase the resolution accuracy for the observation, and the angular distribution of the scattered lights is measured by scanning relatively to the center of the laser beam in a specimen;
   the measuring conditions are defined to provide the scattering volume of 1 $mm^3$ or less or the broadening of the light receiving angle ($\Delta\theta$) by 0.5 deg or less by adjusting the cross sections of the incident laser beam and scattered light.

5. A high-precision scattered light measuring apparatus for evaluating the optical characteristics of transparent materials comprising a laser light source irradiating a laser beam into a specimen, a specimen supporting member fixing the specimen relatively to the laser beam, a scattered light measuring member for measuring the angular distribution of the scattered lights by scanning relatively with the specimen as its center, and beam adjusters for adjusting the cross section of the incident laser beam and the cross section for observing the scattered light, comprising:
   the beam adjusters comprise an incident laser beam adjuster provided in the optical path of the laser beam to adjust the cross section of the laser beam, and a scattered light adjuster provided in the optical path between the specimen and the scattered light measuring member to adjust the cross section for observing scattered light; and
   the beam adjusters define the measuring conditions to provide the scattering volume of 1 $mm^3$ or less or the broadening of light receiving angle of 0.5 deg or less ($\Delta\theta$).

* * * * *